United States Patent
Maier et al.

(10) Patent No.: US 11,940,434 B2
(45) Date of Patent: Mar. 26, 2024

(54) NUTRITION ANALYSIS MODULE FOR A FOOD PROCESSING DEVICE OR FOOD STORAGE DEVICE

(71) Applicant: KONINKLIJKE PHILIPS N.V., Eindhoven (NL)

(72) Inventors: Dieter Johann Maier, Klagenfurt (AT); Raimund Leitner, Klagenfurt (AT); Jozef Pulko, Klagenfurt (AT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 709 days.

(21) Appl. No.: 17/051,199

(22) PCT Filed: May 5, 2019

(86) PCT No.: PCT/EP2019/061473
§ 371 (c)(1),
(2) Date: Oct. 28, 2020

(87) PCT Pub. No.: WO2019/215057
PCT Pub. Date: Nov. 14, 2019

(65) Prior Publication Data
US 2021/0364488 A1   Nov. 25, 2021

(30) Foreign Application Priority Data
May 8, 2018   (EP) ..................................... 18171242

(51) Int. Cl.
*G01N 33/02*   (2006.01)
*A23L 5/00*   (2016.01)
(Continued)

(52) U.S. Cl.
CPC ................ *G01N 33/02* (2013.01); *A23L 5/00* (2016.08); *A23N 1/00* (2013.01); *G01N 21/3577* (2013.01);
(Continued)

(58) Field of Classification Search
CPC ................ G01N 33/02; G01N 21/552; G01N 21/3137; G01N 21/3577; A23L 5/00; A23N 1/00
See application file for complete search history.

(56) References Cited

U.S. PATENT DOCUMENTS

| | | |
|---|---|---|
| 3,902,807 A | 9/1975 | Fleming |
| 4,286,327 A * | 8/1981 | Rosenthal ............ G01N 21/255 250/910 |
| 7,075,645 B2 | 7/2006 | Gehrlein |

(Continued)

FOREIGN PATENT DOCUMENTS

| | | |
|---|---|---|
| DE | 10352924 | 7/2005 |
| DE | 102016008885 | 1/2018 |

(Continued)

OTHER PUBLICATIONS

International Search Report and Written Opinion dated Jul. 10, 2019 for International Application No. PCT/EP2019/061473 Filed May 5, 2019.

*Primary Examiner* — Anthony J Weier
(74) *Attorney, Agent, or Firm* — Maschoff Brennan (57) ABSTRACT

A food processing device or food storage device (70), having: a chamber (72) for housing a foodstuff (42) to be processed or stored; and a nutrition/ingredient analysis system (30), having: an electromagnetic radiation source (32); a radiation guide (34) for guiding the electromagnetic radiation based on total internal reflection (attenuated total reflection, ATR), wherein the radiation guide comprises an input (36) coupled to the electromagnetic radiation source (32), an output (38), and a sensing surface (40) between the input and output for placing against a foodstuff to be analyzed, wherein the sensing surface (40) is for contact with the foodstuff (42); a detector (44) for detecting guided electromagnetic radiation at the output of the radiation guide; and a filter arrangement (46) for wavelength filtering the guided electromagnetic radiation reaching the detector, wherein the (Continued)

filter arrangement includes a plurality of optical bandpass filters (46a, 46b), and the plurality of filters are selectively movable into the path of the detector (44) or there is a respective detector (44a, 44b) for each optical bandpass filter.

12 Claims, 4 Drawing Sheets

(51) Int. Cl.
  *A23N 1/00* (2006.01)
  *G01N 21/3577* (2014.01)
  *G01N 21/552* (2014.01)
  *G01N 21/31* (2006.01)
(52) U.S. Cl.
  CPC ............. *G01N 21/552* (2013.01); *G01N 2021/3137* (2013.01)

(56) References Cited

U.S. PATENT DOCUMENTS

| | | | | |
|---|---|---|---|---|
| 7,840,360 | B1* | 11/2010 | Micheels | G01J 3/42 |
| | | | | 382/142 |
| 2004/0036022 | A1* | 2/2004 | Gore | G01N 21/3563 |
| | | | | 250/339.12 |
| 2013/0275052 | A1 | 10/2013 | Loder | |
| 2015/0276588 | A1 | 10/2015 | Marshall | |
| 2016/0123876 | A1* | 5/2016 | Muldoon | G01N 21/65 |
| | | | | 356/338 |
| 2016/0273960 | A1* | 9/2016 | Perkins | G02B 5/288 |
| 2017/0002976 | A1 | 1/2017 | Wang | |
| 2017/0016813 | A1 | 1/2017 | Wagner | |
| 2017/0029761 | A1 | 2/2017 | Hoffmann-Petersen | |
| 2018/0356341 | A1* | 12/2018 | Muldoon | G01N 33/146 |

FOREIGN PATENT DOCUMENTS

| | | |
|---|---|---|
| EP | 2846160 | 3/2015 |
| FR | 2737571 | 2/1997 |
| JP | S58151542 | 9/1983 |
| JP | H07239300 | 9/1995 |
| JP | H0856565 | 3/1996 |
| WO | 2010042456 | 4/2010 |
| WO | 2013065035 | 5/2013 |
| WO | 2015015493 | 2/2015 |
| WO | 2017051424 | 3/2017 |

* cited by examiner

NUTRITION ANALYSIS MODULE FOR A FOOD PROCESSING DEVICE OR FOOD STORAGE DEVICE

CROSS REFERENCE TO RELATED APPLICATIONS

This application is the U.S. National Phase application under 35 U.S.C. § 371 of International Application No. PCT/EP2019/061473 filed May 5, 2019, which claims the benefit of European Patent Application Number 18171242.3 filed May 8, 2018. These applications are hereby incorporated by reference herein.

FIELD OF THE INVENTION

This invention relates to nutrition analysis of food which is being stored or processed.

BACKGROUND OF THE INVENTION

EP2846160A1 discloses A method for beer fermentation, comprising the steps of: inserting (31) wort and yeast into a vessel (2) to initiate a fermentation process, the wort and yeast forming a vessel content (3); measuring (32), with an on-line measuring device (100), a first extract value (A) that is representative of an extract level (E) of the vessel content (3); automatically controlling (35) a mixing device (6, 7) dependent on the first extract value (A), to withdraw vessel content (3) from the vessel (2) and reinject it into the vessel (2) for effecting mixing of the vessel content (3).

US20130275052A1 discloses that the $CO_2$ content in a liquid, in particular a beverage, is to be tested. Three absorption measurements of the liquid are carried out respectively at a wavelength within a first wavelength range between 4200 and 4300 nm to measure a first absorption value with attenuated total reflectance, at a second wavelength within a second wavelength range between 3950 and 4050 nm and a second absorption value with attenuated total reflectance, and at a third wavelength within a third wavelength range between 3300 and 3900 nm and a third absorption value with attenuated total reflectance. A pre-defined model function is used for determining the $CO_2$ content based on the first, second and third absorption values. The model function is applied to the absorption values and the result of the evaluation is kept available as the $CO_2$ content of the liquid to be tested.

US2015276588A1 discloses that a fluid analyzer includes an optical source and an optical detector defining an optical beam path through an interrogation region of a fluid flow cell. Flow-control devices conduct analyte and reference fluids through a channel and the interrogation region, and manipulate fluid flow in response to control signals to move a fluid boundary separating the analyte and reference fluids across the interrogation region. A controller generates control signals to (1) cause the fluid boundary to be moved across the interrogation region accordingly, (2) sample an output signal from the optical detector at a first interval during which the interrogation region contains more analyte fluid than reference fluid and at a second interval during which the interrogation region contains more reference fluid than analyte fluid, and (3) determine from samples of the output signal a measurement value indicative of an optically measured characteristic of the analyte fluid.

JP H0856565A discloses that to accurately control the state of the fermentation by measuring infrared absorption, etc., of the fermentation broth at a specific infrared absorption frequency of a component whose concentration changes in the course of the fermentation by microorganism. CONSTITUTION: Infrared absorption or a change of infrared absorption of a fermentation broth at a specific infrared absorption frequency of a component (a sugar, an alcohol, etc.), whose concentration changes in the course of the fermentation by microorganism, is measured. Infrared attenuated total reflection spectroscopy (IR-ATR) enables the easy separation of absorption of water from that of the material to be measured and the amount of the material is qualitatively measured without receiving the influence of water.

JP H07239300A discloses that to simultaneously calculate the concns. of a plurality of substances dissolved in an aq. soln. only by performing the measurement of the aq. soln. by an infrared attenuation total reflection method (infrared ATR method) by preliminarily calculating absorptivity at every component in an arbitrary wave number by an infrared ATR method. CONSTITUTION: An absorption wave number peculiar to a substance can be calculated by performing the absorption spectrum analysis of infrared absorptiometric analysis. A wave number region of 900-1200 cm$<-1>$ is an absorption wave number common to saccharides, alcohol or org. acids and different from the absorption wave number of water as the fingerprint region of a substance. The separation of the absorption wave number of water and that of a dissolved substance becomes easy by the use of an infrared ATR method and the taking-out of the absorption of the fingerprint region becomes possible and the quantitative determination of the substance becomes possible. Therefore, a primary formula measuring the substance in a soln. and the relation between absorbancy and concn. in a specific wave number is preliminarily calculated to calculate the absorptivity of the wave number and plural simultaneous equations are solved to calculate the concns. of a plurality of substances dissolved in an aq. soln.

DE10352924A1 discloses a method and an apparatus for qualitative and/or quantitative analysis of substances in liquids, especially in process fluids and/or in alcoholic and non-alcoholic beverages that are in open containers or in closed or sealed containers or containers, on which applied a pressure which is greater than, equal to or less than the atmospheric pressure, wherein the container or containers comprising at least one Behältniswandungs-, top or bottom area and/or a closure that can be pierced, using an integrated in an infrared spectrometer flow cell, enhaltend a ATR crystal. With this measuring device are also liquids present in containers which have an increased internal pressure, analyzed under the actual conditions. Further, the invention relates to a flow cell.

Different nutrition measurement technologies based on near-infrared (NIR) and infrared (IR) light (with or without inclusion of bordering wavelength bands) are in widespread use in laboratories as well as industrial applications.

Miniaturization and cost reduction of the components needed for these technologies bring their application within the reach of consumer applications. Amongst other applications, the determination of the type or composition of some food ingredients is of particular interest, for example the amount of the different macronutrients (carbohydrates, fat, proteins, fibers, water) and micronutrients (vitamins, minerals).

The limitations of miniaturized IR and NIR spectroscopy technology in terms of the spectral resolution (due to size and cost reasons) are addressed by novel mathematical material models and by using cloud-based computation services.

There are thus commercially available NIR spectroscope devices which are able to detect different nutritional components of a sample with a desired accuracy. These devices generally make use of a handheld device, which the user aims at a sample of the foodstuff to be analyzed. The device sends out an infrared light signal and a detector inside the device receives the reflected infrared spectrum. The spectrum data is sent wirelessly (e.g. via BLUETOOTH®) to a mobile device or generally uploaded to a server e.g. over the internet. The mobile device sends the spectrum data via the internet to a server system which analyzes the spectrum. The analysis outcome information is sent back to the mobile device which shows the outcome to the user.

The user is then informed which kind of nutritional components are in the scanned food.

This arrangement works for solid foodstuff samples but it needs special adaptations to be usable with liquid foods like blended or juiced fruits or vegetables. Because the device is handheld, the investigated food item will be scanned in a different way each time so that the received spectra will be different for the same food type, giving a limitation to the accuracy. The spectroscopic information in the NIR wavelength region comprises the $2^{nd}$ to $4^{th}$ harmonics of the fundamental vibrations in the IR wavelength region.

The analysis is also very complex, requiring a large amount of data processing, such that the analysis needs to be performed on an external server. The broad and overlapping features in the NIR spectrum require complex mathematical pattern recognition algorithms, usually executed on servers and accessed via the internet. A measurement approach using the fundamental vibrations in the IR spectrum allow easier processing and analyses without cloud computation and more precise and selective analysis results. The data has to be transferred to a server and a lot of data has to be transferred back and interpreted so that the user can read the information. Some foodstuffs also cannot be analyzed reliably, such as cloudy juices.

There is therefore a need for an analysis system for food being stored or processed, which enables accurate results for a liquid foodstuff and which can be implemented with low cost and complexity, operable without complex algorithms requiring cloud computing.

SUMMARY OF THE INVENTION

The invention is defined by the claims.

According to examples in accordance with an aspect of the invention, there is provided a food processing device or food storage device, comprising:
a chamber for housing a foodstuff to be processed or stored; and
a nutrition analysis system, comprising:
an electromagnetic radiation source;
a radiation guide for guiding the electromagnetic radiation based on total internal reflection, wherein the radiation guide comprises an input coupled to the electromagnetic radiation source, an output, and a sensing surface between the input and output for placing against a foodstuff to be analyzed, wherein the sensing surface is for contact with the foodstuff; and
a detector for detecting guided electromagnetic radiation at the output of the radiation guide.

The analysis method implemented by this device is based on evanescent absorbance which takes place in conjunction with total internal reflections, when the radiation travels along the radiation guide. The absorption characteristics of the foodstuff influence the power loss caused by this evanescent absorption, which in turn correlates with the attenuation of the electromagnetic radiation before it is detected by the detector. Thus, the system operates using attenuated total reflectance (ATR). The level of detected guided electromagnetic radiation is dependent on the nature of the foodstuff. In this way, the analysis system may be implemented on one side only of a foodstuff, instead of requiring radiation generation on one side and detection on the other side. It also creates more repeatable results, since manual relative positioning between the analysis system and the foodstuff is avoided. The ATR approach avoids the need for narrow cavities, as are required by conventional IR sensing due to the high absorption coefficient of water.

The chamber may house the foodstuff in a static manner, or it may be part of an in-line food processing system in which the foodstuff is only temporarily present.

The sensor surface is placed for direct contact with the foodstuff to be analyzed. In this way, the foodstuff directly influences the evanescent field, thus giving optimum sensitivity of the system to the constituents of the foodstuff. By using a sensing surface, an average of the volume of the foodstuff influencing the evanescent field is used for the measurement. This gives more stable measurement than a point like measurement area.

The detection process implements wavelength selectivity. For example, the device preferably also comprises a filter arrangement for wavelength filtering the guided electromagnetic radiation reaching the detector.

Various detector and filter combinations are possible such as two or more detectors with discrete filters, one detector with a (spatially) moving filter or a tunable filter, or two or more filters and a spatially moving detector.

The detection is based on the absorption of the foodstuff at a particular wavelength (or a multitude or range of wavelengths). The imaginary part of the refractive index of the foodstuff describes the wavelength-dependent absorption. ATR may require the real part of the refractive index of the sensing surface material to be in a specific range.

The filter arrangement for example comprises at least one optical bandpass filter. A bandpass filter is able to select a narrow frequency band which is of interest for a particular nutrient target.

The filter arrangement for example comprises a plurality of optical bandpass filters, wherein the plurality of filters are selectively movable into the path of the detector or there is a respective detector for each optical bandpass filter. This enables multiple different nutrient targets to be analyzed.

More generally, a filter may be used with any suitable specific characteristic, for which a bandpass filter is one example. Some applications may need more complex filter characteristics or for cost reasons this could be preferable instead of having several bandpass filters.

The use of discrete filters avoids the need for a full spectrometer. This gives a cost-efficient implementation which may be suitable for integration into a consumer product.

It is noted that instead of providing a filter arrangement, the wavelength selection may be implemented at the source (by emitting a desired wavelengths) or within the detector (by having selective sensitivity to a desired wavelength).

The device may be a storage vessel such as a food container, jar, bottle or flask for keeping food warm or cold, or it may be a food processing device such as a mixer, blender or juicer.

The sensing surface may be integrated into a wall of the chamber. By integrating the system into a chamber wall, a low cost and compact sensing system is provided. It may be used to identify nutritional information for dietary purposes, or identification of food types, or for the purposes of identifying whether a foodstuff is fresh or perished.

The sensing surface may however be at any location which comes into contact with the foodstuff, for example at any location along a food processing path for a food processing device.

The electromagnetic radiation source for example comprises an infrared or near infrared radiation source with a wavelength in the range 0.2 to 20 μm, for example in the range 8 to 10 μm. Wavelengths in the near infrared and infrared band are able to be used to identify particular nutrients, such as glucose or fructose.

The radiation guide may comprise a crystal. It may have a high refractive index to provide total internal reflection of the electromagnetic radiation. It may for example comprise germanium, diamond, KRS-5, zinc selenide, silicon or a combination of (layered) materials.

The device may further comprise a collimating lens or a reflector at the output of the electromagnetic radiation source for controlling the angular spread of radiation provided to the radiation guide.

This may be used to ensure that all of the radiation provided to the radiation guide undergoes total internal reflection and hence propagates efficiently to the detector.

A focusing lens or a reflector may also or instead be used at the input to the detector. This may be used to ensure that all of the radiation emitted from the guide efficiently reaches the detector.

A chopper may also be provided (for example at the input to the detector). Many cost-effective detectors cannot detect DC signals so a chopper (mechanical or electrical) may be used to create an AC signal (or the source may instead be electrically modulated/pulsed). The frequency is typically in the range 1 to 10 Hz. Some detectors are able to detect DC signals so the chopper/modulation is a requirement only for some detectors.

A data communication system may be provided for wirelessly transferring data based on the detector output to a remote device. This enables the nutritional information to be provided to a user in a most convenient way, for example by connecting to an app hosted on a smart phone. Of course, a wired system is also possible, or else the device may have the required output device to function as a user interface, such as a screen.

The chamber may be for containing a liquid foodstuff. The analysis of liquid foodstuffs has previously been particularly problematic. The invention provides a reliable and low cost solution, by relying on the full contact between the liquid (because it can flow) and the sensing surface, which gives fully repeatable sensing results.

The device may comprise a blender, juicer, soup maker or cooker. These are examples of food processing devices which may incorporate the analysis system. A juice extraction device for example comprises a masticator. The device in general could be any kitchen appliance or food processing device.

Alternatively, the device may comprise a storage jar or bottle. The storage jar or bottle may be for long term storage or for short term transportation (for example a flask) For long-term storage, the analysis may then be used to determine when the contained foodstuff is becoming perished.

The detector may be adapted to detect in at least two wavelength ranges, a relatively narrow measurement range and relatively broad reference range.

In principle a setup with just one wavelength is possible if a calibration is performed prior to each measurement. However, using two ranges mitigates aging and long-term drifting effects. A factory calibration may then be used.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a food processing device or food storage device in which a foodstuff stored or processed in a chamber is analyzed by an integrated nutrition analysis system which uses attenuated total reflection (ATR) with nutrient/ingredient selectivity, for example by means of one or more discrete filters.

Figure 1:
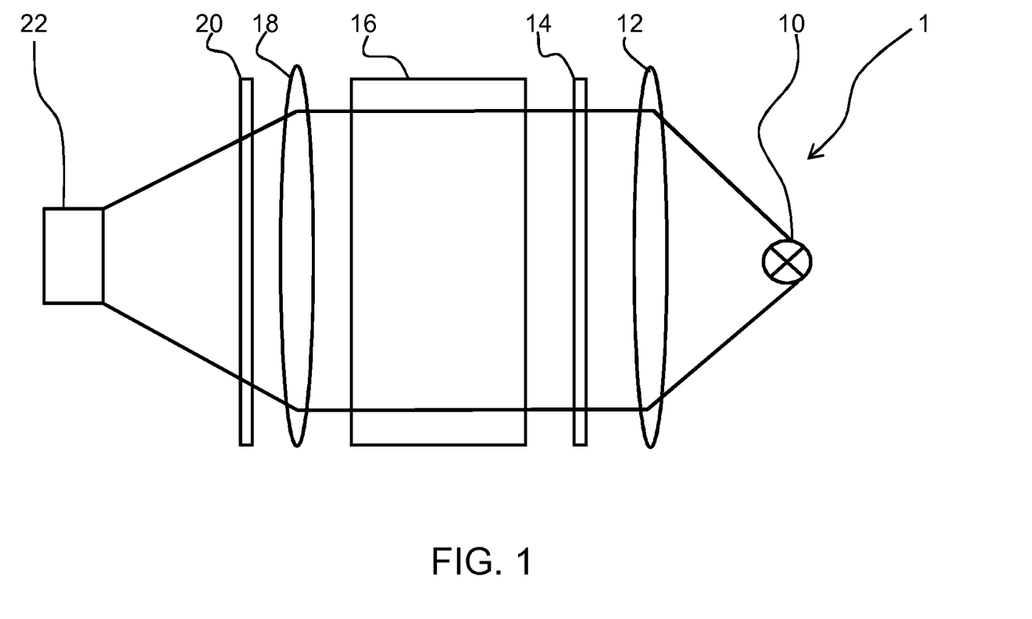
FIG. 1 shows how transmission through a liquid may be used for nutrient analysis.

FIG. 1 shows how transmission through a liquid may be used for nutrient analysis. The analysis system 1 shown in FIG. 1 comprises an infrared source 10, a collimating lens 12, a filter 14, the liquid sample 16, a focusing lens 18, a chopper 20 and a detector 22.

The infrared light source 10 sends out infrared light with a specific wavelength range. The infrared light penetrates the prepared foodstuff (e.g. fruit juice). Specific ingredients absorb infrared light at specific wavelengths. Depending which kind of ingredient is to be analyzed or detected, a specific wavelength filter 14 is used. The infrared detector 22 measures the absolute value of the specific wavelength after the filter. For some ingredients it may be necessary to measure more than one wavelength.

Depending how much IR light in this specific wavelength (band) is absorbed, more or less IR light reaches the detector. A voltage or current level is detected for recording the light reaching the detector. Note that the filter 14 can also be located at the detector side instead of the source side.

To detect more different ingredients, more filters have to be used. For example, distinguishing between two ingredients requires two different filters, and the ingredients absorb the infrared light in different bands.

Depending of the mechanical integration the collimating lens 12 and/or the focusing lens 18 are needed to guide the infrared light correctly. There may be multiple lenses. Some detector types may need the chopper element 20 to provide an AC signal for detection. The frequency is typically in the range 1 to 10 Hz. Signal modulation at the light source may be used instead of providing a chopper further downstream.

The main disadvantage of this measurement setup is that the cloudiness of some liquid samples, for example caused by fibers and other particles, falsifies the optical measurement result. The natural liquids extracted from fruits and vegetables are generally cloudy and contain suspended particles. Furthermore, this arrangement is for use in the NIR range, where the features are broad and overlapping and hence less selective than in the IR range.

Figure 2:
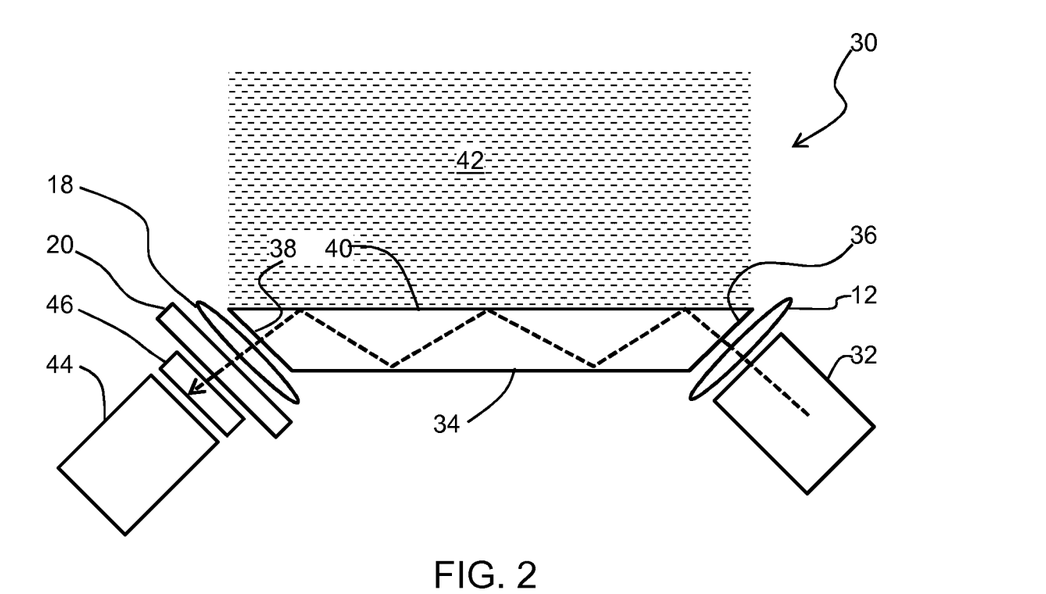
FIG. 2 shows the principle of operation of a nutrient analysis system of an example of the invention.

FIG. 2 shows the principle of operation of a nutrient analysis system of the invention, which is to be integrated into a kitchen device, and operates based on attenuated total reflection (ATR).

The nutrition analysis system 30 comprises an electromagnetic radiation source 32, a radiation guide 34 for guiding the electromagnetic radiation based on total internal reflection, wherein the radiation guide comprises an input 36 coupled to the electromagnetic radiation source 32, an output 38, and a sensing surface 40 between the input and output for placing against a foodstuff to be analyzed. The sensing surface 40 is for contact with a foodstuff 42 to be analyzed.

The electromagnetic radiation source 32 comprises an infrared or near infrared radiation source with a wavelength in the range 1 to 20 μm, for example in the range 8 to 10 μm. Wavelengths in the near infrared and infrared band are able to be used to identify particular nutrients, such as glucose.

The radiation guide 34 comprises a crystal. It has a high refractive index to provide total internal reflection of the electromagnetic radiation. It may for example comprise germanium, diamond, KRS-5, zinc selenide, silicon or a combination of (layered) materials.

Suitable materials for ATR spectroscopy will be known to those skilled in the art.

A detector 44 is for detecting guided electromagnetic radiation at the output of the radiation guide 34. A filter arrangement 46 is used for wavelength filtering the guided electromagnetic radiation reaching the detector. It may be at the input side or the output side of the guide 34.

The filter arrangement 46 comprises at least one optical bandpass filter. A bandpass filter is able to select a narrow frequency band which is of interest for a particular nutrient target. The use of one or more discrete bandpass filters avoids the need for a full spectrometer. This gives a cost-efficient implementation which may be suitable for integration into a consumer product.

The analysis is based on evanescent absorbance which takes place in conjunction with total internal reflections, when the radiation travels along the radiation guide. The absorption characteristics of the foodstuff influence the power loss caused by this evanescent absorption, which in turn correlates with the attenuation of the electromagnetic radiation before it is detected by the detector. Thus, the system operates using attenuated total reflectance (ATR).

The analysis system 30 is on one side only of the foodstuff 42 and thus does not rely on transmission through the foodstuff. It also gives more repeatable results since the direct contact with the foodstuff avoids manual positioning differences.

FIG. 2 also shows the optional use of the collimating lens or reflector arrangement 12 of FIG. 1, the focusing lens or reflector arrangement 18 of FIG. 1 and the chopper 20 of FIG. 1.

Various detector 44 and filter 46 combinations are possible, so that multiple wavelengths may be detected.

Figure 3:
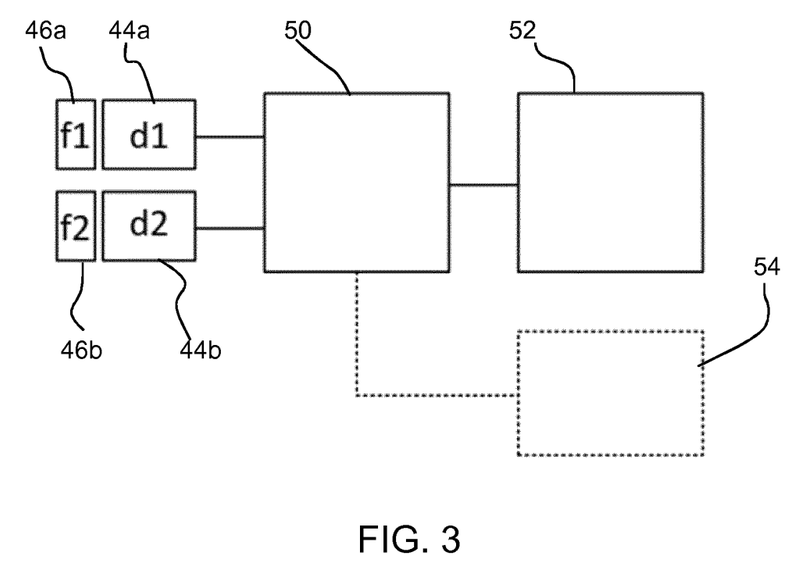
FIG. 3 shows a first example of detector and filter combination.

FIG. 3 shows a first example, based on two detectors 44a, 44b each with their own respective filter 46a, 46b. The detector signals are provided to a processor 50, which drives a user interface 52 as well as providing transmission of data over a wireless connection module 54. There may be two or more detectors. The output voltages or currents of each detector represent different ingredients.

Figure 4:
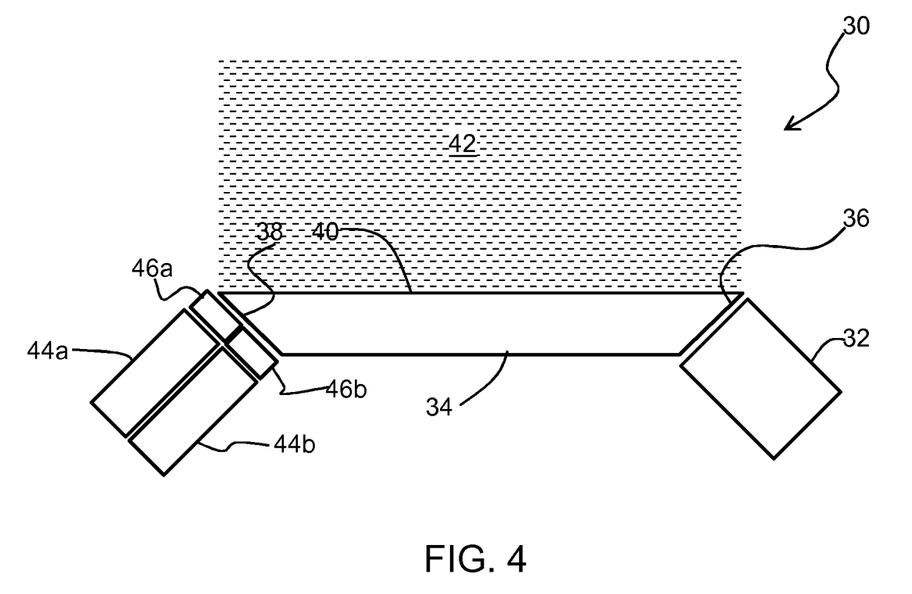
FIG. 4 how the example of FIG. 3 may be implemented.

FIG. 4 how the example of FIG. 3 may be implemented. The two filters and detector share the output 38 of the guide 34.

Figure 5:
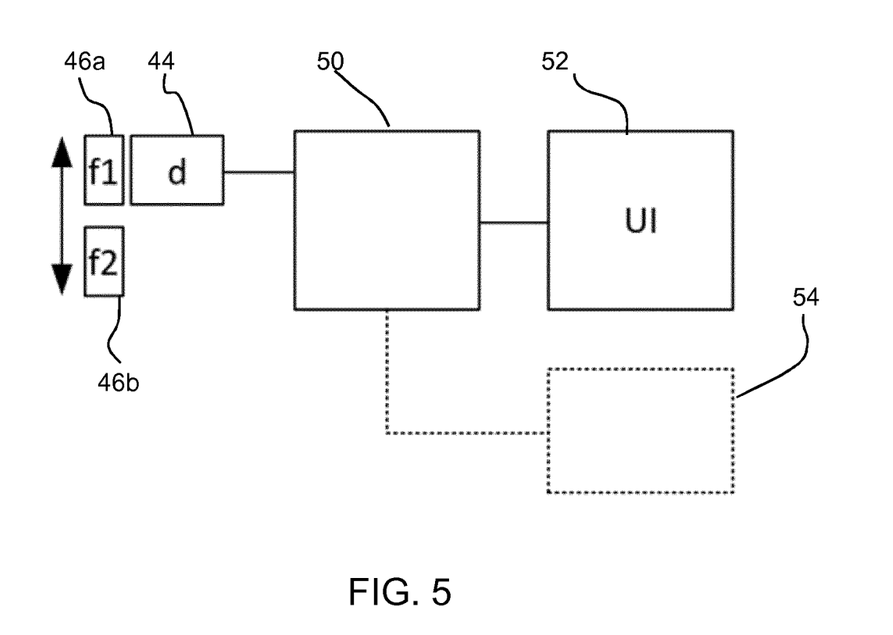
FIG. 5 shows a second example of detector and filter combination.

FIG. 5 shows a second example, based on a single detector 44 and a movable filter arrangement of two filters 46a, 46b. The detector signals are again provided to a processor 50, which drives a user interface 52 as well as providing transmission of data over a wireless connection module 54. Only one detector output is measured. For example, filter 46a may be mechanically switched in front of the detector so that the output voltage or current of the detector represents one specific ingredient. When filter 46b is switched in front of the detector then the output voltage or current of the detector is represents another specific ingredient.

Figure 6:
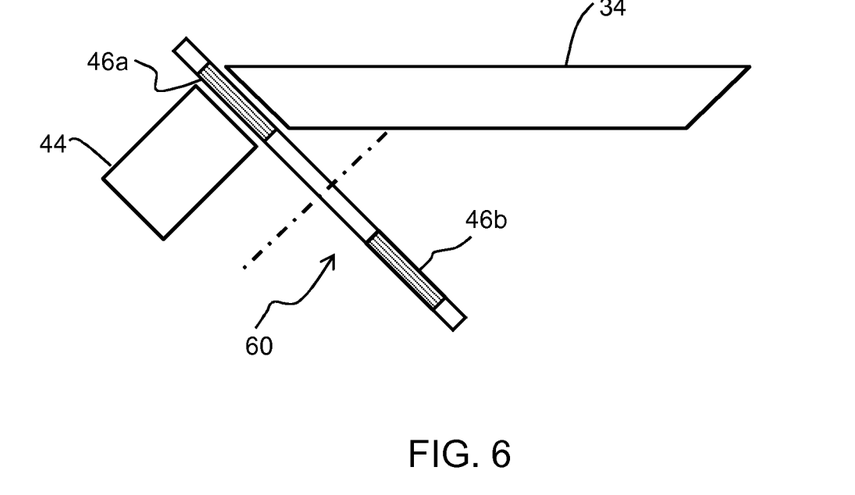
FIG. 6 how the example of FIG. 5 may be implemented.

FIG. 6 how the example of FIG. 5 may be implemented. The two filters 46a, 46b are part of a rotating filter arrangement 60. The variable filter function may be established in different ways, for example a linear reciprocating filter may be used. An alternative is a mirror or lens arrangement which is used to reflect the optical path from one detector to the other. The filters can also be part of a sensor module, and one or more sensors as well as one ore more filters can be packaged into such a sensor module.

The invention is based on the integration of the nutrition analysis system described above into a kitchen device, and in particular a kitchen device in the form of a food processing device or food storage device, comprising a chamber for housing a foodstuff to be processed or stored.

Figure 7:
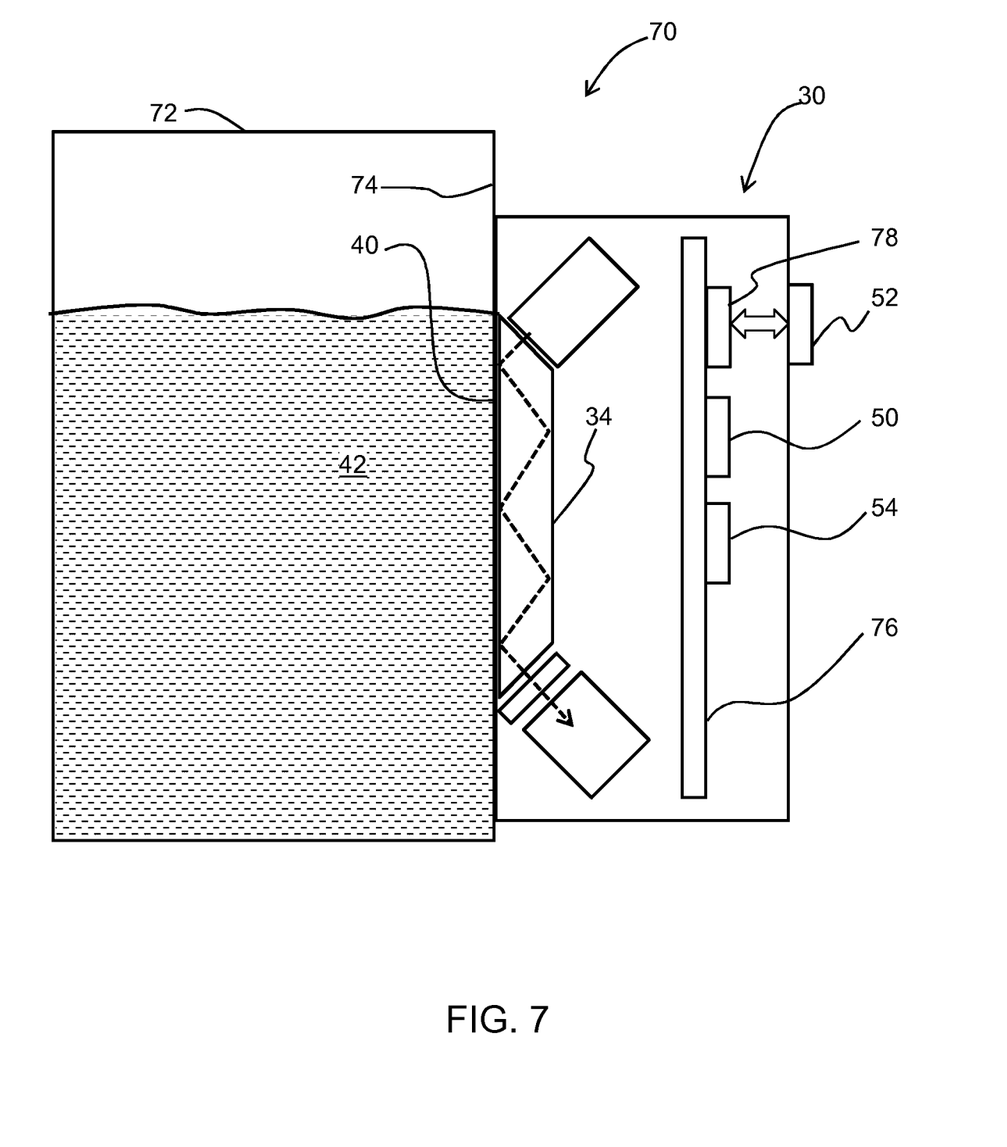
FIG. 7 shows an example of a device having a chamber and a nutrient analysis system.

FIG. 7 shows an example of a device 70 having a chamber 72 and a nutrient analysis system 30 as described above. The chamber 72 may house the foodstuff in a static manner, as may be the case for a storage tin, jar, bottle or other vessel, or it may be part of an in-line food processing system in which the foodstuff is only temporarily present. Thus, the chamber may be part of a juicer, blender, soup maker, cooker etc.

The sensor surface 40 is placed for direct contact with the foodstuff to be analyzed. For example, an exposed internal portion of a wall 74 of the chamber may be defined by the sensing surface 40 of the radiation guide 34. This enables the desired direct contact between the foodstuff 42 and the radiation guide of the analysis system. In this way, the foodstuff directly influences the evanescent field, thus giving optimum sensitivity of the system to the constituents of the foodstuff. By using a sensing surface, an average of the volume of the foodstuff influencing the evanescent field is used for the measurement. This gives more stable measurement than a point like measurement area.

The sensing surface 40 may however be at any location which comes into contact with the foodstuff, for example at any location along a food processing path for a food processing device. The geometry of the crystal may be optimized to work preferably in terms of selectivity/signal strength with selected detector/source combinations.

The device 70 further comprises a circuit board 76 which carries the processor 50, wireless connection module 54 and a user interface circuit 78 for controlling the external user interface 52 (e.g. touch screen, control buttons etc.). The analysis module is typically battery operated.

The invention may be used to provide immediate nutrient information for processed food (such as juiced food) or to provide nutrient information over time for a storage jar or bottle. The information may then be used to determine when the foodstuff is becoming perished.

In addition to operating at different wavelengths for different food nutrients, a wavelength range may be used as a calibration reference. A broad reference frequency range may be used to compensate for aging and long-term drifting effects. A factory calibration may then be used.

Examples of nutrients which may be detected and their associated wavelengths are sugars: glucose 9.67 µm, fructose 9.39 µm.

Other candidates are saccharose, lactose, fats/lipids, starch, etc. Any nutrition relevant molecule with a reasonably distinct IR-spectrum (and hence selectable with affordable filters) could be measured. It may be necessary to determine potential overlaps with other constituents in the foodstuff.

The sensing surface for example has an area of tens to thousands of mm$^2$, and a thickness of 1 mm order of magnitude. A miniaturized integrated combination of detector, crystal and source (e.g. in one package) may have considerable smaller mechanical dimensions (for example formed as a wafer-level package).

As explained above, the arrangement of FIG. 2 (as used in the device of FIG. 7) may include the collimating lens or reflector arrangement 12 of FIG. 1 and/or the focusing lens or reflector arrangement 18 of FIG. 1 and/or the chopper 20 of FIG. 1. These components are not shown in FIGS. 3 to 7 to keep the figures simple.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A food processing device or food storage device, comprising:
a chamber for housing a foodstuff to be processed or stored; and
a nutrition analysis system, comprising:
an electromagnetic radiation source;
a radiation guide for guiding electromagnetic radiation based on total internal reflection, wherein the radiation guide comprises an input coupled to the electromagnetic radiation source, an output, and a sensing surface between the input and the output for placing against the foodstuff to be analyzed, wherein the sensing surface is for contact with the foodstuff;
a detector for detecting guided electromagnetic radiation at the output of the radiation guide; and
a filter arrangement for wavelength filtering the guided electromagnetic radiation reaching the detector, wherein the filter arrangement comprises a plurality of optical bandpass filters, and wherein the plurality of optical bandpass filters are selectively movable into a path of the detector.

2. The device as claimed in claim 1, wherein the sensing surface is integrated into a wall of the chamber.

3. The device as claimed in claim 1, wherein the electromagnetic radiation source comprises an infrared or near infrared radiation source with a wavelength in the range 0.2 to 20 µm.

4. The device as claimed in claim 1, wherein the radiation guide comprises:
a crystal; or
a layer structure.

5. The device as claimed in claim 1, further comprising a collimating lens or collimating reflector at an output of the electromagnetic radiation source for controlling the angular spread of radiation provided to the radiation guide.

6. The device as claimed in claim 1, further comprising a focusing lens or focusing reflector at the output of the radiation guide for focusing radiation to the detector.

7. The device as claimed in claim 1, further comprising a chopper.

8. The device as claimed in claim 1, further comprising a data communication system for wirelessly transferring data based on an output from the detector to a remote device.

9. The device as claimed in claim 1, wherein the chamber is for containing a liquid foodstuff.

10. The device as claimed in claim 1, further comprising a blender, juicer, soup maker, or cooker.

11. The device as claimed in claim 1, further comprising a storage jar or bottle.

12. The device as claimed in claim 1, wherein the detector is adapted to detect in at least two wavelength ranges, a relatively narrow measurement range and relatively broad reference range.

* * * * *